US005654172A

United States Patent [19]
Li et al.

[11] Patent Number: 5,654,172
[45] Date of Patent: Aug. 5, 1997

[54] GABA$_A$ RECEPTOR EPSILON SUBUNIT

[75] Inventors: Yi Li, Gaithersburg; Ewen F. Kirkness, Olney, both of Md.

[73] Assignee: Human Genome Sciences, Inc., Rockville, Md.

[21] Appl. No.: 459,100

[22] Filed: Jun. 2, 1995

[51] Int. Cl.$^6$ .................... C12P 21/06; C12N 15/00; C12N 1/20; C07H 21/04
[52] U.S. Cl. ............... 435/69.1; 435/172.1; 435/252.33; 435/320.1; 536/23.5; 935/22; 935/23; 935/73
[58] Field of Search ................... 435/69.1, 172.1, 435/252.33, 320.1; 536/235; 935/22, 23, 73

[56] References Cited

U.S. PATENT DOCUMENTS

| | | | |
|---|---|---|---|
| 5,166,066 | 11/1992 | Carter et al. | 435/240.2 |
| 5,182,290 | 1/1993 | Albaugh | 514/293 |
| 5,286,860 | 2/1994 | Blum et al. | 544/230 |

OTHER PUBLICATIONS

PCT International Search Report.
Bureau et al.; The Journal of Biological Chemistry; vol. 267; No. 12, Issue of Apr. 25, 1992 pp. 8679–8684.
Whiting, et al.; Proc. Natl. Acad. Sci., vol. 87, pp. 9966–9970; Dec. 1990.
Ymer et al.; the EMBO Journal vol. 9 No. 10, pp. 3261–3267; 1990.
Garrett et al.; Biochemical and Biophysical Research Communications, pp. 1039–1045, vol. 156, No. 2; 1988.
Shivers et al.; Neuron, vol. 3, 327–337; Sep. 1989.
Pritchett et al.; Reports; Science, vol. 245; Sep. 1989.
Current Protocols in Microbiology; Supplement 14, 1990.
Luddens et al.; Letters to Nature, vol. 346; 16 Aug. 1990; pp. 648–651.
McKernan et al.; Neuron, vol. 7, 667–676; Oct. 1991.
Ymer et al.; The EMBO Journal, vol. 8, No. 6, pp. 1665–1670; 1989.

*Primary Examiner*—Mindy Fleisher
*Assistant Examiner*—Bonnie D. Weiss
*Attorney, Agent, or Firm*—J. G. Mullins; Elliot M. Olstein

[57] ABSTRACT

Disclosed is a human GABA$_A$ epsilon subunit receptor and DNA (RNA) encoding such polypeptides (RNA). Also provided is a procedure for producing such polypeptides by recombinant techniques and agonists and antagonists for such polypeptides. Also provided are methods of using the agonists, for example, to treat anxiety, Huntington's Chorea, muscular spasms and rigidity, and sleep and seizure disorders. Antagonists may be used, for example, to diagnose and treat anxiety, Huntington's Chorea, sleep and seizure disorders, Alzheimer's disease, Parkinson's disease and overdoses with benzodiazepine and for enhancing cognition and reversing sedation after application of general anesthesia during surgery. Also disclosed are diagnostic methods for detecting mutations in the polynucleotides of the present invention and for detecting levels of the soluble polypeptides in samples derived from a host.

19 Claims, 12 Drawing Sheets

FIG. 1A

```
               10                        30                          50
GGGACAGGGGCTGAGGAGGATGAGGAGAACCCTGGGACCCAGAAGACCGTGCCCTTGCCCGGAA
                          70                        90                       110
GTCCTGCCTGTAGGGCTTGAAGGACTTGCCCTAACAGAGCCTCAACAACTACCTGGTGATT
               130                       150                       170
CCTACTTCAGCCCCTTGGTGTGAGCAGCTTCTCAACATGAACTACAGCCTCCACTTGGCC
                                                     M  N  Y  S  L  H  L  A
               190                       210                       230
TTCGTGTGTCTGAGTCTCTTCACTGAGAGAATGTGCATCCAGGGAGTCAGTTCAACGTC
 F  V  C  L  S  L  F  T  E  R  M  C  I  Q  G  S  Q  F  N  V
               250                       270                       290
GAGGTCGGCAGAAGTGACAAGCTTTCCCTGCCTTGAGAACCTGACTGGCTGACTCTGGAC
 E  V  G  R  S  D  K  L  S  L  P  G  F  E  N  L  T  A  G  Y
               310                       330                       350
AACAAATTTCTCAGGCCCAATTTTGGTGGAGAACCCGTACAGATAGCGCTCAGTTCAACGTC
 N  K  F  L  R  P  N  F  G  G  E  P  V  Q  I  A  L  T  L  D
               370                       390                       410
ATTGCAAGTATCTCTAGCATTTCAGAGAGTAACATGGACTACACAGCCACCATATACCTC
 I  A  S  I  S  S  N  M  D  Y  T  A  T  I  Y  L
               430                       450                       470
CGGACAGGCGCTGGATGGACCAGCGGCTGGTGTTTGAAGGCAACAAGAGCTTCACTCTGGAT
 R  Q  R  W  M  D  Q  R  L  V  F  E  G  N  K  S  F  T  L  D
               490                       510                       530
GCCCGGCTCGTGGAGTTCCTCTGGGTGCCAGATACTTACATTGTGGAGTCCAAGAAGTCC
 A  R  L  V  E  F  L  W  V  P  D  T  Y  I  V  E  S  K  K  S
               550                       570                       590
TTCCTCCATGAAGTCACTGTGGGAAACAGGCTCATCCGCCTCTTCTCCAATGGCACGGTC
 F  L  H  E  V  T  V  G  N  R  L  I  R  L  F  S  N  G  T  V
```

FIG. 1B

```
       610                           630                              650
CTGTATGCCCCTCAGAATCACGACAACTGTTGCATGTAACATGGATCTGTCTAAATACCCC
 L  Y  A  L  R  I  T  T  T  V  A  C  N  M  D  L  S  K  Y  P
                   670                            690                              710
ATGGACACAGACATGCAAGTTGCAGCTGGAAAGCTGGGGCTATGATGGAAATGATGTG
 M  D  T  Q  T  C  K  L  Q  L  E  S  W  G  Y  D  G  N  D  V
                   730                            750                              770
GAGTTCACCTGGCTGAGAGGAACGACTCTGTGCGTGGACTGGAACACCTGCGGCTTGCT
 E  F  T  W  L  R  G  N  D  S  V  R  G  L  E  H  L  R  L  A
                   790                            810                              830
CAGTACACCATAGAGCGGTATTTCACCTTAGTCACCAGATCGCAGCAGGAGACAGGAAAT
 Q  Y  T  I  E  R  Y  F  T  L  V  T  R  S  Q  Q  E  T  G  N
                   850                            870                              890
TACACTAGATTGGTCTTACAGTTTGAGCTTCGGAGGAATGTTCTGTATTTCATTTTGGAA
 Y  T  R  L  V  L  Q  F  E  L  R  R  N  V  L  Y  F  I  L  E
                   910                            930                              950
ACCTACGTTCCTTCCACTTTCCTGGTGGTGTTGTCCTGGGTTTCATTTTGGATCTCTCTC
 T  Y  V  P  S  T  F  L  V  V  L  S  W  V  S  F  W  I  S  L
                   970                            990                              1010
GATTCAGTCCCTGCAAGAACCTGCATTGGAGTGACGACCGTGTTATCAATGACCACACTG
 D  S  V  P  A  R  T  C  I  G  V  T  T  V  L  S  M  T  T  L
                   1030                           1050                             1070
ATGATCGGGTCCCGCACTTCTCTCCCAACACCAACTGCTTCATCAAGGCCATCGATGTG
 M  I  G  S  R  T  S  L  P  N  T  N  C  F  I  K  A  I  D  V
                   1090                           1110                             1130
TACCTGGGGATCTGCTTTAGCTTTGTGTTTGGGGCTTGCTAGAATATGCAGTTGCTCAC
 Y  L  G  I  C  F  S  F  V  F  G  A  L  L  E  Y  A  V  A  H
```

FIG. 1C

```
         1150                                    1170                          1190
TACAGTTCCTTACAGCAGATGGCAGCAGCCAAAGATAGGGGACAACAAGGAAGTAGAAGAA
 Y   S   S   L   Q   Q   M   A   A   A   K   D   R   G   T   T   K   E   V   E   E
                 1210                                    1230                          1250
GTCAGTATTACTAATATCATCAACAGCTCCATCTCCAGCTTTAAACGGAAGATCAGCTTT
 V   S   I   T   N   I   I   N   S   S   I   S   S   F   K   R   K   I   S   F
                 1270                                    1290                          1310
GCCAGCATTGAAATTTCCAGCGACAACGTTGACTACAGTGACTTGACAATGAAAACCAGC
 A   S   I   E   I   S   S   D   N   V   D   Y   S   D   L   T   M   K   T   S
                 1330                                    1350                          1370
GACAAGTTCAAGTTTGTCTTCCGAGAAAAGATGGGCAGGATTGTTGATTATTCACAATT
 D   K   F   K   F   V   F   R   E   K   M   G   R   I   V   D   Y   F   T   I
                 1390                                    1410                          1430
CAAAACCCCAGTAATGTTGATCACTATTCCAAACTACTGTTTCCTTTGATTTTTATGCTA
 Q   N   P   S   N   V   D   H   Y   S   K   L   L   F   P   L   I   F   M   L
                 1450                                    1470                          1490
GCCAATGTATTTTACTGGGCATACTACTACATGTATTTTGAGTCAATGTTAAATTTCTTGCA
 A   N   V   F   Y   W   A   Y   Y   Y   M   Y   F   *
                 1510                                    1530                          1550
TGCCATAGGTCTTCAACAGGACAAGATAATGATGTAAATGGTATTTTAGGCCAAGTGTGC
                 1570                                    1590                          1610
ACCCCACATCCAATGGTGCTACAAGTGACTGAAATAATATTTGAGTCTTTCTGCTCAAAGA
                 1630                                    1650
ATGAAGCTCCAACCATTGTTCTAAGCTGTG
```

FIG. 2

MNYSLHLAFVCLSLFTERMCIQGSQFNVEVGRSDKLSLPGFENLTAGYNKFLRPNFGGEPVQ
IALTLDIASISSISESNMDYTATIYLRQRWMDQRLVFEGNKSFTLDARLVEFLWPDTYIVE
SKKSFLHEVTVGNRLIRLFSNGTVLYALRITTTVACNMDLSKYPMDTQTCKLQLESWGYDGN
DVEFTWLRGNDSVRGLEHLRLAQYTIERYFFTLVTRSQQETGNYTRLVLQFELRRNVLYFILE
TYVPSTFLVVLSWVSFWISLDSVPARTCIGVTTVLSMTTLMIGSRTSLPNTNCFIKAIDVYL
GICFSFVFGALLEYAVAHYSSLQQMAAKDRGTTKEVEEVSITNIINSSISSSFKRKISFASIE
ISSDNVDYSDLTMKTSVKFKFVFREKMGRIVDYFTIQNPSNVDHYSKLLFPLIFMLANVFYW
AYYMYF

```
- L X L L S L - P X F T X X X C X X X - S X X X  Majority
            |                   |
           30                  40                  50

- L A F V C L - S L F T E R M C I Q G - S Q F N    HTPAN40.PRO
I L L L S L Y P G F T S Q K S D D D Y E D Y A      GABA-R.g2
- L G L L S F - - P V M I T M V C A H - S T N E    Hu.GABA-Beta1.pep Y D X X L R P D F G G X P V X I X X X D V A S      Majority
            |                   |
           80                  90                 100

Y N K F L R P N F G G E P V Q I A L T L D I A S    HTPAN40.PRO
Y D N K L R P D D I G V K P T L I H T D M Y V N S  GABA-R.g2
Y D I R L R P D F G G P P V D V G M R I D V A S    Hu.GABA-Beta1.pep X F X G X X X X L T L D X R X V X X L W V P D T    Majority
            |                   |
          130                 140                 150

V F E G N K - S F T L D A R L V E F L W V P D T    HTPAN40.PRO
K F N S T I K V L R L N S N M V G K I W I P D T    GABA-R.g2
S Y S G I P L N L T L D N R V A D Q L W V P D T    Hu.GABA-Beta1.pep
```

```
       T V L Y X L R I T T T A A C X M D L X X Y P M D   Majority
            180            190           200
       T V L Y A L R I T T T V A C N M D L S K Y P M D   HTPAN40.PRO
       R V L Y S L R L T I D A E C Q L H N F P M D       GABA-R.g2
       T V L Y G L R I T T T A A C M M D L R R Y P L D   Hu.GABA-Beta1.pep X X V X G X X X R L X Q F S I V X Y X X X X X X   Majority
            230            240           250
       D S V R G L E H L R L A Q Y T I E R Y F T L V T   HTPAN40.PRO
       V E V G D T R S W R L Y Q F S F V G L R N T T E   GABA-R.g2
       G A V T G V N K I E L P Q F S I V D Y K M V S K   Hu.GABA-Beta1.pep L Q T Y X P S T L I V V L S W V S F W I N X D A   Majority
            280            290           300
       L E T Y V P S T F L V V L S W V S F W I S L D S   HTPAN40.PRO
       I Q T Y I P C T L I V V L S W V S F W I N K D A   GABA-R.g2
       L Q T Y M P S T L I T I L S W V S F W I N Y D A   Hu.GABA-Beta1.pep
```

```
          330              340              350
SLPKXX-YVKAIDXYLXXCFXFVFXA  Majority SLPNTNCF-YVKVS-YVTAMDLFVSVCFIFVFSA  HTPAN40.PRO
SLPKVS-YVTAMDLFVSVCFIFVFSA         GABA-R.g2
TLPKIP-YVKAIDIYLMGCFVVFLA          Hu.GABA-Beta1.pep 380              390              400
XXXXXIXNXXSXXXXQXXXXXIXX  Majority EVEEVSITNIINSSISSFKR--KISF  HTPAN40.PRO
KNPAPTIDIRPRSATIQMNNATH---  GABA-R.g2
QDQSANEKNKLEMNKVQVDAHGNILL  Hu.GABA-Beta1.pep 430              440              450
XFXXXXX--XRXXXXXXXXXY---  Majority --FKFV-----FREKMGRIVDY---           HTPAN40.PRO
FFCCFEDC---------------             GABA-R.g2
MYSYDSASIQYRKPLSSREAYGRALD          Hu.GABA-Beta1.pep
```

GABA$_A$ RECEPTOR EPSILON SUBUNIT

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human GABA$_A$ receptor. The invention also relates to inhibiting the action of such polypeptides.

Gamma-aminobutyric acid (GABA) is the major inhibitory neurotransmitter in the mammalian central nervous system. The major type of receptor for the inhibitory neurotransmitter GABA, called the GABA$_A$ receptor (GABA$_A$), is a member of a gene superfamily of ligand-gated ion channels. GABA, the endogenous ligand for the GABA$_A$ complex, stimulates chloride ion conductance through the associated chloride ion channel. The predominant effect of GABA is the interaction with a specific receptor protein which results in an increase of the chloride ion conductance of the post-synaptic membrane to produce an inhibition of neuronal firing. GABA is found in many central neurons (e.g., basal ganglia, cerebellum). GABA is derived from glutamate, which is decarboxylated by glutamic acid decarboxylase. After interaction with receptors, GABA is actively "pumped" back into the prejunctional neurons.

The GABA$_A$ receptor is a multi-subunit ligand-gated ion channel. This receptor is a heterooligomeric protein composed of several distinct polypeptide types. Five different classes of subunit have been defined, $\alpha$, $\beta$, $\gamma_1$, $\delta_\lambda$ and $\rho$. Molecular cloning of these polypeptides reveals that they show 20–40% identity with each other, and 10–20% identity with polypeptides of the nicotinic acetylcholine receptors and strychnine-sensitive glycine receptor. Each subunit class is also represented by a family of genes whose members have 60–80% amino acid sequence identity. Sequences of 6 $\alpha$, 3 $\beta$, 3 $\gamma$, 1 $\delta$ and 2 $\rho$ subunits have been reported. Regions of conserved and variable amino acid sequence suggests structural and functional domains within each polypeptide. All of the polypeptides when expressed in heterologous cells produce GABA-activated chloride channels, and different subunit combinations express different pharmacological properties. The distributions of mRNAs for the different GABA$_A$ receptor polypeptides and their subtypes show significant brain regional variation consistent with pharmacological and biochemical evidence for receptor heterogeneity. Subpopulations of GABA$_A$ receptors with different cellular and regional locations show different sensitivity to GABA, to modulators like steroids, to physiological regulation, to disease processes and to pharmacological manipulation by drugs such as benzodiazepines. The properties of the different subpopulations of GABA$_A$ receptors are determined by which of the one or more different subunits are expressed in a given cell to produce a variety of different oligomeric protein structures.

The GABA$_A$ receptor chloride-ionophore complex is the primary site of action for many of the drugs used to treat anxiety and seizure disorders such as the benzodiazepines and anticonvulsant barbiturates. By allosteric drug-induced modulation the receptors serve as molecular control elements through which the levels of anxiety, vigilance, muscle tension and epileptic activity can be regulated.

The present inventors have found a new class of GABA$_A$ subunit. This new GABA$_A$ subunit may be responsible for similar and additional pharmacological events as the other classes of GABA$_A$ subunit.

In accordance with one aspect of the present invention, there is provided a novel mature polypeptide which is a GABA$_A$ receptor epsilon subunit, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there are provided agonists against such GABA$_A$ receptor epsilon subunits and a process for utilizing such agonists for therapeutic purposes, for example, to diagnose and treat anxiety, Huntington's Chorea and sleep and seizure disorders.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of Alzheimer's disease, Parkinson's disease, overdoses with benzodiazepine drugs, and other neurological disorders and to enhance memory.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A, 1B and 1C (FIG. 1A illustrates the first portions of the polynucleotide sequence encoding the human GABA$_A$ receptor epsilon subunit protein with its deduced amino acid sequence and FIGS. 1B and 1C consecutively continue with the second and third parts, respectively, to the end of the same polynucleotide and amino acid sequences) collectively show the cDNA SEQ ID NO:1 and corresponding deduced amino acid sequence SEQ ID NO:2 of GABA$_A$ receptor epsilon subunit. The full length protein is 440 amino acid residues with the first 24 amino acids representing the putative leader sequence such that the mature protein comprises 416 amino acid residues.

FIG. 2 illustrates the amino acid sequence for GABA$_A$ receptor epsilon subunit where the standard one letter abbreviation for amino acids is used. The putative transmembrane domains are underlined.

Figure 3A:
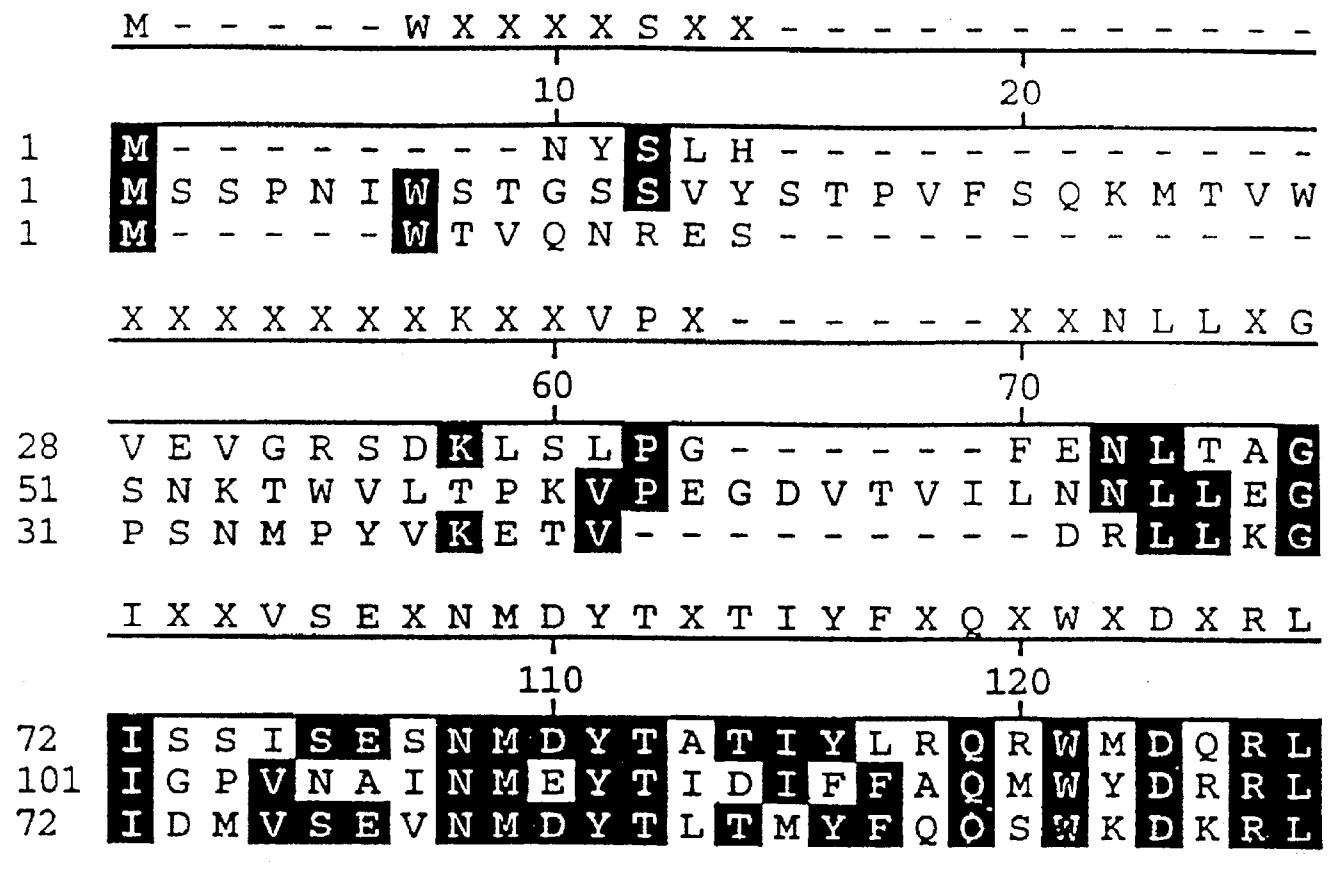
Figure 3C:
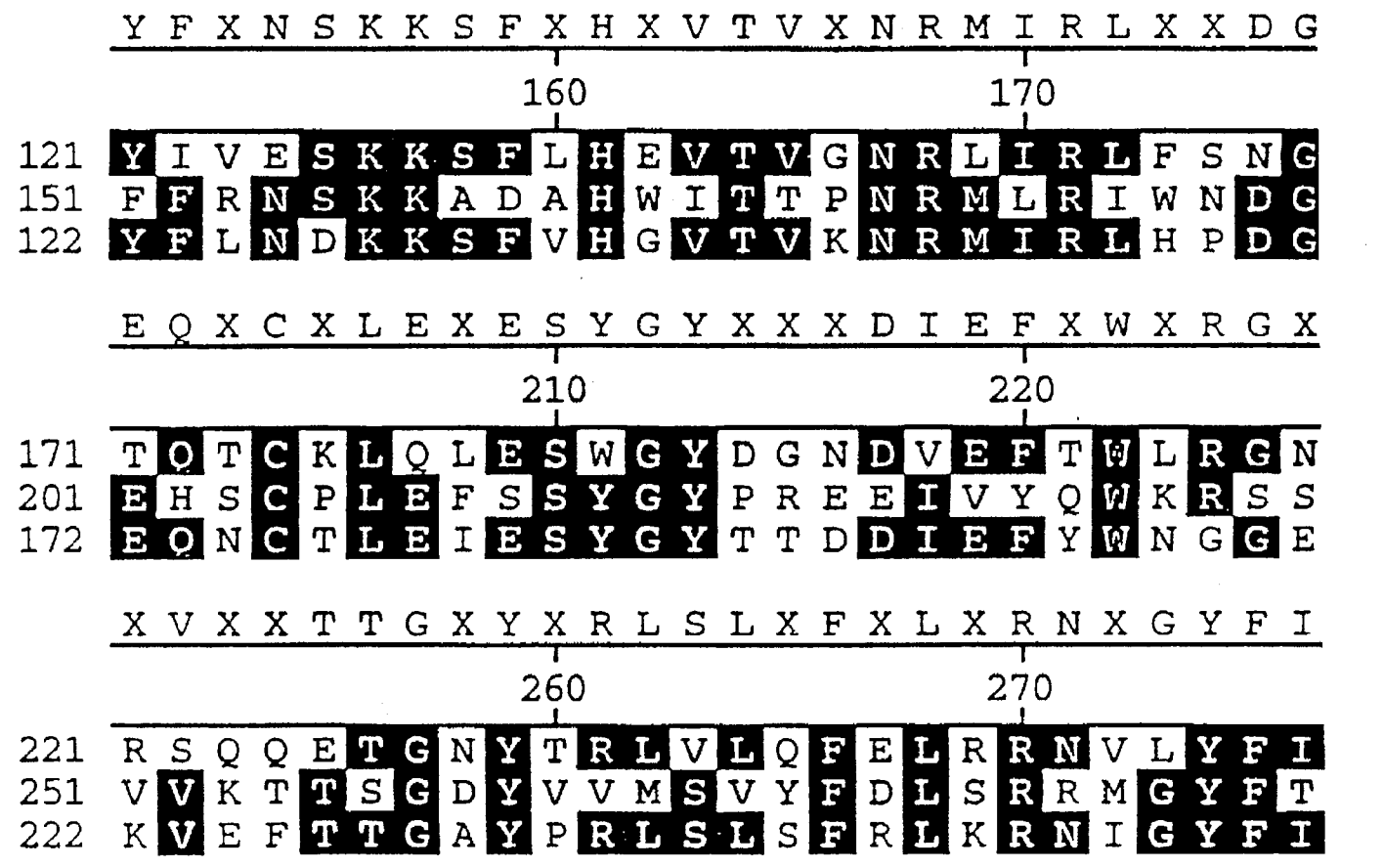
Figure 3E:
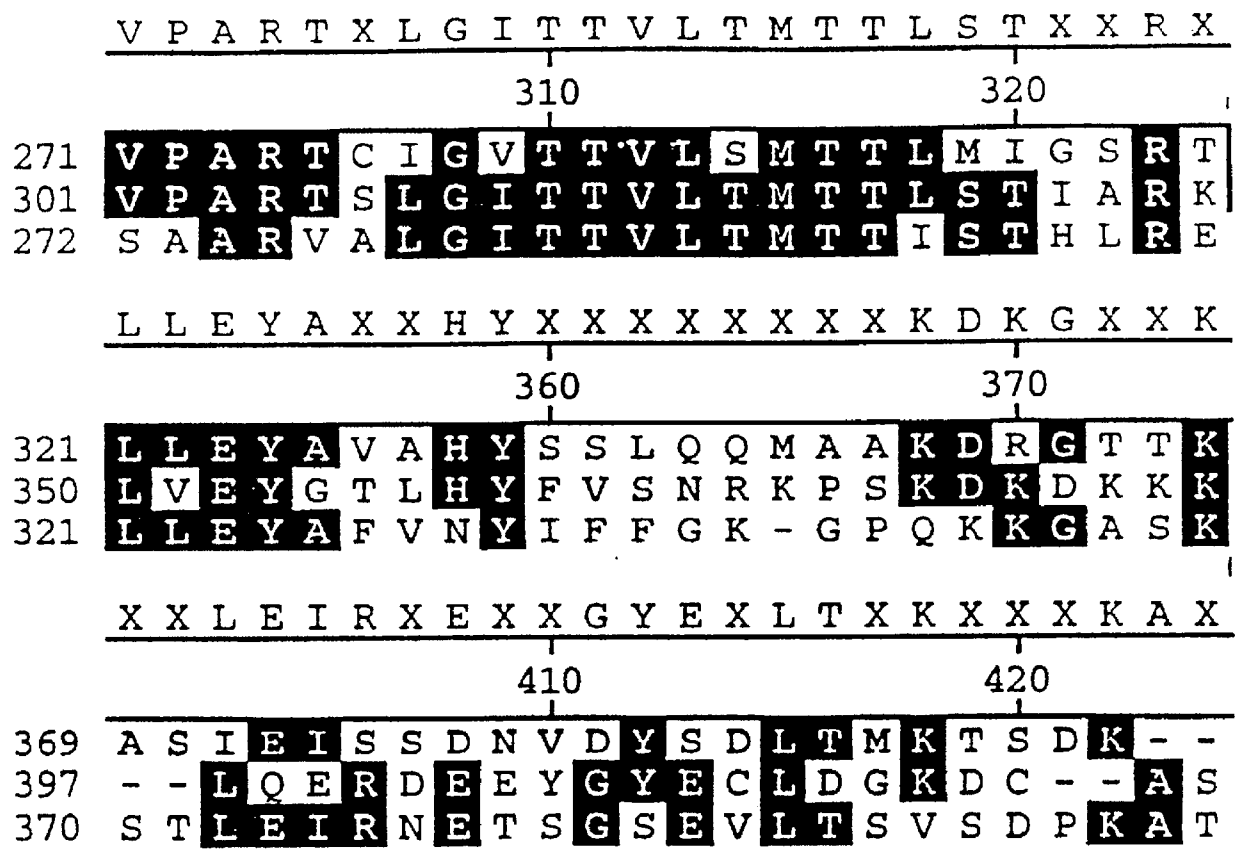
Figure 3G:
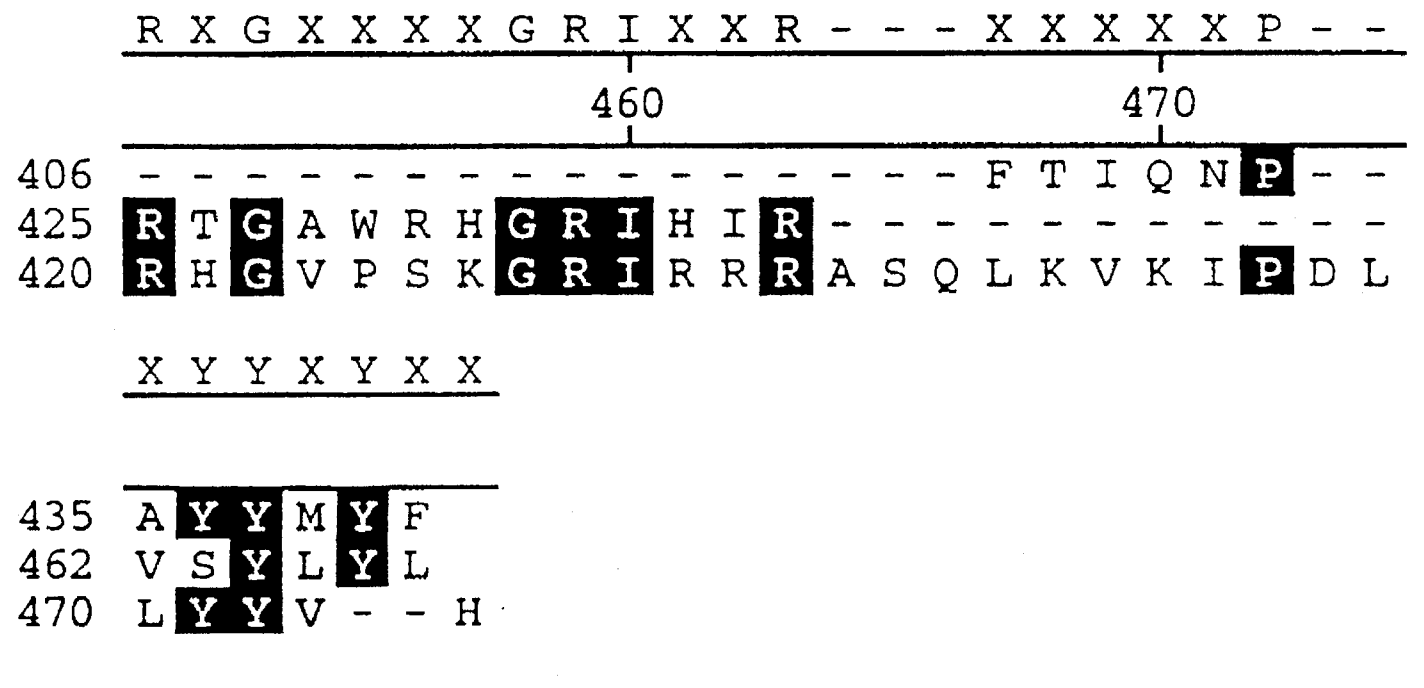

FIGS. 3A–3H collectively show polypeptide sequences in alignment and consecutively present the alignment of the sequences to illustrate an amino acid sequence comparison of the GABA$_A$ receptor epsilon subunit (HTPAN40.PRO amino acid sequence (SEQ ID NO:2); first line in each row of the sequence comparison) with the amino acid sequences of two other GABA$_A$ receptor subunits (GABA-R.g2 (SEQ ID NO:3) and Hu. GABA-Beta1.pep (SEQ ID NO:4); second and third lines, respectively, in each row of the sequence comparison). One-letter abbreviations are utilized for the amino acid residues and shaded residues match exactly in at least two of the three amino acid sequences show. Exact-match amino acid residues are illustrated in each comparative row by a line above the HTPAN40.PRO sequence line labelled as "Majority" at the end of each row. The portions of the amino acid sequence (of SEQ ID NO:2) shown in the first comparative line of FIG. 3 and the comparative amino acid sequences (SEQ ID NOS:3 and 4, respectively) shown at comparative lines 2 and 3 of FIG. 3 are represented by one-letter amino acid codes. A line above the comparative sequences repeats the one-letter codes that are highlighted as being common to all three polypeptide sequences, however such is not a sequence, per se, and is merely a redundant representation of the highlighted portions of the sequence of SEQ ID NO:2, for example.

Figure 3H:
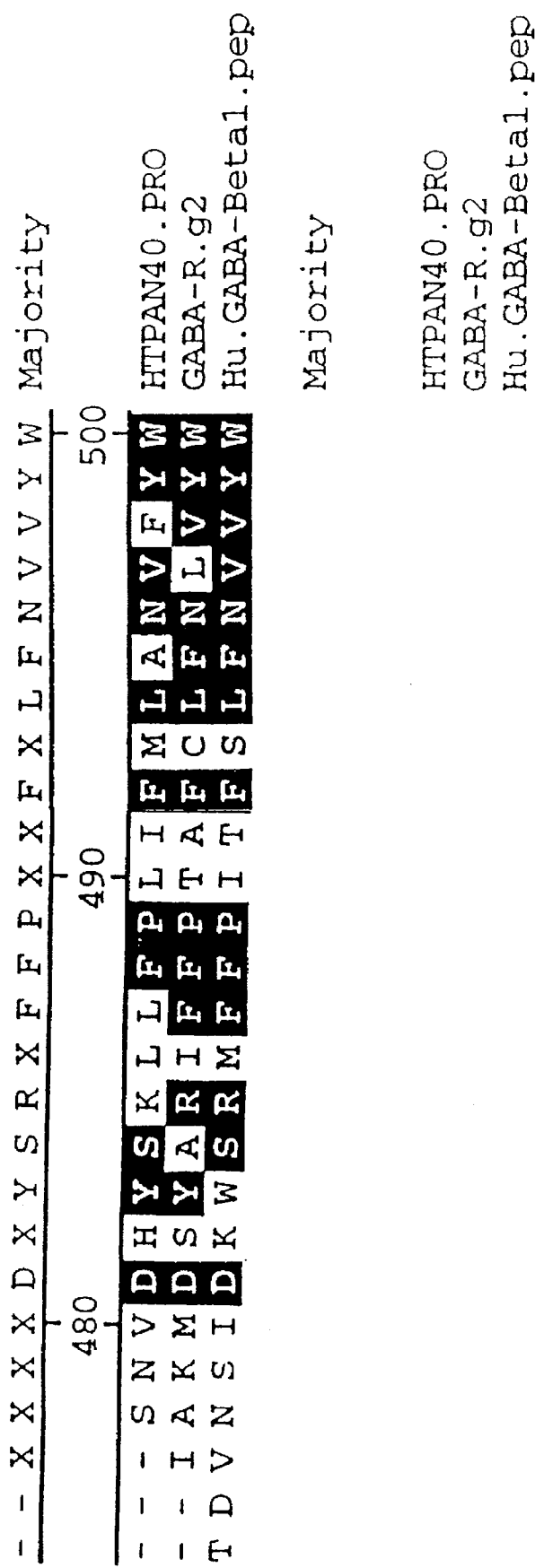

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75810 on Jun. 10, 1994.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

The polynucleotide of this invention was discovered in a cDNA library derived from pancreas tumor. It is structurally related to the GABA$_A$ subunit receptor family. It contains an open reading frame encoding a protein of about 440 amino acid residues of which approximately the first 24 amino acids residues are the putative leader sequence such that the mature protein comprises 416 amino acids. The protein exhibits the highest degree of homology to rat GABA$_A$ receptor epsilon Beta-1 subunit with 50% identity and 70% similarity over a 400 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1C, collectively, (SEQ ID NO:1) or that of the deposited clone or may be a different coding sequence which coding sequence, as a result of the redundancy or degeneracy of the genetic code, encodes the same mature polypeptide as the DNA of FIGS. 1A–1C, collectively, (SEQ ID NO:1) or the deposited cDNA.

The polynucleotide which encodes for the mature polypeptide of FIGS. 1A–1C, collectively, (SEQ ID NO:2) or for the mature polypeptide encoded by the deposited cDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1C, collectively, (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIGS. 1A–1C, collectively, (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1C, collectively, (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS 1A–1C, collectively, (SEQ ID NO:1) or the deposited cDNA (s), i.e. function as a soluble receptor by retaining the ability to bind the ligands for the receptor even though the polypeptide does not function as a membrane bound receptor, for example, by eliciting a second messenger response.

Alternatively, the polynucleotides may have at least 20 bases, preferably 30 bases and more preferably at least 50 bases which hybridize to a polynucleotide of the present invention and which have an identity thereto, as hereinabove described, and which may or may not retain activity. For example, such polynucleotides may be employed as probes for the polynucleotide of SEQ ID NO:1, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

Fragments of the genes may be employed as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a receptor polypeptide which has the deduced amino acid sequence of FIGS. 1A–1C, collectively, (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–1C, collectively, (SEQ ID NO:2) or that encoded by the deposited cDNA, means a polypeptide which either retains substantially the same biological function or activity as such polypeptide, i.e. functions as a receptor, or retains the ability to bind the ligand for the receptor even though the polypeptide does not function as a G-protein coupled receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1C, collectively (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also includes portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "gene" means the segment of DNA involved in producing a polypeptide chain; it includes regions preceding and following the coding region "leader and trailer" as well as intervening sequences (introns) between individual coding segments (exons).

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudo-rabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the $E.\ coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.\ coli$.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as $E.\ coli$, Streptomyces, *Salmonella typhimurium;* fungal cells, such as yeast; insect cells such as Drosophila and Spodoptera Sf9; animal cells such as CHO, COS or Bowes melanoma; adenovirus; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM47. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of $E.\ coli$ and $S.\ cerevisiae$ TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein coupled receptors of the present invention may be employed in a process for screening for compounds which activate (agonists) or inhibit activation (antagonists) of the receptor polypeptide of the present invention.

In general, such screening procedures involve providing appropriate cells which express the receptor polypeptide of the present invention on the surface thereof. Such cells include cells from mammals, yeast, drosophila or *E. Coli*. In particular, a polynucleotide encoding the receptor of the present invention is employed to transfect cells to thereby express the G-protein coupled receptor. The expressed receptor is then contacted with a test compound to observe binding, stimulation or inhibition of a functional response.

One such screening procedure involves the use of melanophores which are transfected to express the G-protein coupled receptor of the present invention. Such a screening technique is described in PCT WO 92/01810 published Feb. 6, 1992.

Thus, for example, such assay may be employed for screening for a compound which inhibits activation of the receptor polypeptide of the present invention by contacting the melanophore cells which encode the receptor with both the receptor ligand and a compound to be screened. Inhibition of the signal generated by the ligand indicates that a compound is a potential antagonist for the receptor, i.e., inhibits activation of the receptor.

The screen may be employed for determining a compound which activates the receptor by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in Science, volume 246, pages 181–296 (October 1989). For example, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding the G-protein coupled receptor into Xenopus oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

G-protein coupled receptors are ubiquitous in the mammalian host and are responsible for many biological functions, including many pathologies. Accordingly, it is desirous to find compounds and drugs which stimulate the G-protein coupled receptor on the one hand and which can inhibit the function of a G-protein coupled receptor on the other hand.

For example, compounds which activate the G-protein coupled receptor may be employed for therapeutic purposes, such as the treatment of asthma, Parkinson's disease, acute heart failure, hypotension, urinary retention, and osteoporosis.

In general, compounds which inhibit activation of the G-protein coupled receptor may be employed for a variety of therapeutic purposes, for example, for the treatment of hypertension, angina pectoris, myocardial infarction, ulcers, asthma, allergies, benign prostatic hypertrophy and psychotic and neurological disorders, including schizophrenia, manic excitement, depression, delirium, dementia or severe mental retardation, dyskinesias, such as Huntington's disease or Gilles dila Tourett's syndrome, among others. Compounds which inhibit G-protein coupled receptors have also been useful in reversing endogenous anorexia and in the control of bulimia.

An antibody may antagonize a G-protein coupled receptor of the present invention, or in some cases an oligopeptide, which bind to the G-protein coupled receptor but does not elicit a second messenger response such that the activity of the G-protein coupled receptors is prevented. Antibodies include anti-idiotypic antibodies which recognize unique determinants generally associated with the antigen-binding site of an antibody. Potential antagonist compounds also include proteins which are closely related to the ligand of the G-protein coupled receptors, i.e. a fragment of the ligand, which have lost biological function and when binding to the G-protein coupled receptor, elicit no response.

An antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of G-protein coupled receptor. The antisense RNA oligonucleotide hybridizes to the mRNA in vivo and blocks translation of mRNA molecules into G-protein coupled receptor (antisense-Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

A small molecule which binds to the G-protein coupled receptor, making it inaccessible to ligands such that normal biological activity is prevented, for example small peptides or peptide-like molecules, may also be used to inhibit activation of the receptor polypeptide of the present invention.

A soluble form of the G-protein coupled receptor, e.g. a fragment of the receptors, may be employed to inhibit activation of the receptor by binding to the ligand to a polypeptide of the present invention and preventing the ligand from interacting with membrane bound G-protein coupled receptors.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

Another example is the patch clamp assay. The DNA encoding the $GABA_A$ epsilon subunit is inserted into a HEK 293 cell. The DNA sequence is inserted into an expression cassette, preferably into an expression plasmid. As used herein "expression cassette" refers to DNA sequences necessary for expression of coding sequence in eukaryotic cells. An example of a plasmid is pCDM8 which is commercially available and preferred.

Plasmids containing a selectable marker gene may be cotransfected with plasmids containing DNA sequences that encode the $GABA_A$ epsilon subunit. $GABA_A$ receptors are gated channels which, upon binding GABA, allow chloride ions to pass into the cell. The $GABA_A$ receptor will allow GABA to open the channel and let more chloride into the cell if the molecule being tested is an agonist or less chloride ions into the cell if the molecule being tested is an antagonist. The amount of chloride ions that pass through the $GABA_A$ receptor epsilon submit can be directly measured using the patch clamp assay. This assay measures the charge flow into and out of an electrode sealed on the surface of a cell. The flow of chloride ions entering the cell is measured as a function of the current that leaves the cell to maintain electrical equilibrium within the cell as the gate opens. The patch assay is fully described in Hamill, O. P. et al., Improved Patch Clamp Techniques for High Resolution Current Recording from Cells and Cell-Free Membrane Patches, *Pfluegers Arch.*, 391:85–100 (1981).

Using the patch clamp assay, the effect a compound has on a receptor incorporated in the stable cell line can be determined. The range of sensitivity of the whole cell patch clamp assay is about 1000 pA and allows for the distinguishing of currents of between 2 and 5 pA.

The $GABA_A$ epsilon subunit polypeptide of the present invention may be employed for identifying other subunits of the $GABA_A$ receptor. An example of a procedure for identifying these subunits comprises raising high titer polyclonal antisera against unique, bacterially expressed $GABA_A$ epsilon polypeptides. These polyclonal antisera are then used to immunoprecipitate detergent-solubilized $GABA_A$ receptors from a mammalian brain preferably a rat brain. Also, preferably the hippocampus section of the brain is used.

The agonists and antagonists identified above may be employed as therapeutic agents. Agonists are used to mimic the effects of GABA at the $GABA_A$ receptor and therefore increase the inhibitory effects. These agonists are therefore useful for treating anxiety, Huntington's Chorea, muscular spasms and rigidity, and sleep and seizure disorders. The antagonists block the inhibition mediated by the receptor and therefore increase neuronal firing and are therefore useful for the treatment of Alzheimer's disease, Parkinson's disease and overdoses with benzodiazepine. Antagonists may also be employed for enhancing cognition and for reversing sedation after application of general anesthesia during surgery.

The agonists and antagonists of the present invention may be employed in combination with a suitable pharmaceutical carrier. Such compositions comprise a therapeutically effective amount of the agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the agonists and antagonists of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes, including intra-anal for specifically treating epilepsy. The pharmaceutical compositions are administered in an amount which is effective for treating and/or prophylaxis of the specific indication. The amounts and dosage regimens of the compositions administered to a subject will depend on a number of factors such as the mode of administration, the nature of the condition being treated and the judgment of the prescribing physician. In general, the compositions are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The agonists or antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

This invention also provides a method of detecting expression of a receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., Nature, 324:163-166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., PNAS, USA, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to receptor proteins. Unattached reporter antibody is then washed out. Peroxidase substrates are then added to the dish and the amount of color developed in a given time period is a measurement of the amount of receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Expression of Recombinant $GABA_A$ receptor epsilon subunit in HEK 293 cells

A fragment of the cDNA encoding $GABA_A$ receptor epsilon subunit was cloned into a vector using the CMV immediate early promoter to drive transcription of the gene. The vector, pCDM8, is available from by Invitrogen Corporation, San Diego, Calif. 92121. The cDNA fragment was inserted into the plasmid by first digesting the plasmid with HindIII and XbaI (blunted) and ligating the cDNA at those sites in the plasmid. Plasmid DNA was prepared by the alkaline lysis procedure (Maniatis, T., E. F. Fritsch, and J. Sambrook, 1989, Molecular Cloning: A Laboratory Manual. Cold Spring Harbor Laboratory, Cold Spring Harbor, N.Y.) followed by two cycles of CsCl equilibrium density gradient centrifugation.

Transfection protocol used to transfect HEK 293 cells (HeLa cells may also be transfected) was adapted from Chen, C., and H. Okayama, 1987. High Efficiency Transformation of Mammalian Cells by Plasmid DNA. Mol. Cell. Biol. 7:2745–2752 (Chan-Okayama $CaPO_4$ pH 6.95 techniques). A stock solution of 2.5M $CaCl_2$ (Mallinckrodt) was prepared, filter sterilized through a 0.45 μm-pore-size nitrocellulose filter (Nalge) and stored at −20 degree(s) C. Then 2X Bes-buffered saline (2XBBS) containing 50 mM Bes (pH 6.95), 280 mM NaCl, and 1.5 mM $Na_2 HPO4$ was prepared, filter sterilized, and stored at −20 degree(s) C. N,N-bis(2-hydroxyethyl)-2-aminoetrane-sulfonic acid (BES) was obtained from Sigma. The pH was adjusted with HCl at room temperature. HEK293 cells (American Type Culture Collection, CRL 1573) were maintained in MEM (Gibco) supplemented with 10% Fetal Bovine Serum (Gibco), penicillin-streptomycin (Gibco), and glutamine (Gibco), in a 5% $CO_2$, 37 degree(s) C. Forma Scientific Incubator.

Exponentially growing HEK 293 cells were removed with trypsin-EDTA, plated at a density of $1.5 \times 10^6$ cells per 10 cm plate, and incubated overnight at 5% $CO_2$, 37 degree(s) C in 10 mls of growth medium. For selection purposes 1 μg of a plasmid pWL0Neo (Stratagene) containing the aminoglycoside phosphotransferase (neo) gene driven by the thymidine kinase promoter was used per 10 cm dish containing $1 \times 10^6$ cells. Plasmid DNA was mixed with 50 mu 1 of 2.5M $CaCl_2$ and brought to a final volume of 0.5 ml with water. This mixture was added to 0.5 ml of 2× BBS and incubated for 90 seconds at room temperature. This resulting calcium phosphate-DNA solution was added (1 ml volume) to the plate of cells, swirled gently, and incubated for 15–24 hours at 37 degree(s) C. under 3% $CO_2$. The media was removed, the cells were rinsed two time with MEM media, and rinsed with fresh MEM+10% Fetal Bovine Serum. The cells were incubated for 48 hours at 37 degree(s) C under 5% $CO_2$.

Forty-eight hours after transfection the cells were trypsenized and split (1:8) into four plates. They were grown under selective pressure of growth media containing 1 mg/ml G418 sulfate (Gibco) at 1 mg/ml and grown for 2 weeks until colonies appeared. Selection of stable transformants took approximately 15–20 days. Colonies were separated into 24 well dishes and used after sufficient growth in G418 selective media to seed two 10 cm dishes. After sufficient growth in the 10 cm dishes, one was used to prepare total RNA; cells in the remaining dish were cryopreserved for possible future plating. The RNA was analyzed by Northern blotting.

To determine the frequency of stable transformation, the cells were transfected, as described. At the point when the cells were split and plated under selective pressure (G418 sulfate), cells were also plated, in duplicate, at a density of $1-3 \times 10^3$ cells per 10 cm plate. One set of plates was maintained in nonselective growth medium, while the duplicate plates were grown in growth media with G418 sulfate (a mg/ml). Control plates were maintained in nonselective media 5–7 days; the colonies were then stained and counted. To determine the number of $Neo^+$ transformants, cells were maintained under selective pressure for 2–3 weeks; the colonies were then stained and counted. The transformation efficiency is expressed as a % transformation. This is determined by dividing the number of $Neo^r$ colonies by the number of colonies grown in nonselective medium and multiplying the result by 100.

Clones from the transfected plasmids were tested for the expression of functional channels. These tests were carried out by patch-clamp electrophysiology of whole cells. The whole-cell configuration of patch clamp technique was used to record the GABA-mediated Cl-currents in human embryonic kidney cells transfected with $GABA_A$ receptor epsilon subunits. Patch pipettes were made of borosilicate glass with a resistance of 0.5 to 2 megaohms. The cell was bathed in the buffer medium containing (mM) NaCl 135, KCl 5, $MgCl_2$ 1, $CaCl_2$ 1.8 and Hepes 5, pH 7.2. The pipette was filled with the solution containing (mM) CsCl140, EDTA 11, ATP 2, $MgCl_2$ 4 and Hepes 10, pH 7.3. The holding potential was −60 mV. The bathing solution containing 5 μM $GABA_A$ with or without test drug was applied to the cell through a U-tube positioned about 100 microns away from the cell.

EXAMPLE 2

Baculovirus expression of $GABA_A$ Receptor Epsilon Subunit

A general method for expression of other $GABA_A$ receptor subunits has been described previously (Carter, D. B., et al., Bio/Technology, 10:679–681 (1992)). In this example, SF-9 cells (approximately $10^6$ cells) are infected with baculovirus constructs (approximately $10^8$ pfu), which express the epsilon subunit. Cells might also be co-infected with combinations of baculovirus constructs that express the epsilon subunit and other known $GABA_A$ receptor subunits. The infected SF-9 cells are harvested after 60 hours. The cells are used for electrophysiological recordings (see example 1) or for radioligand binding assays. For the latter, cells are broken in a solution containing 118 mM NaCl, 5 mM KCl, 20 mM HEPES-Tris, pH 7.3, with a Polytron homogenizer. Unbroken cells and nuclei aggregates are removed by centrifugation at 1000 g for 10 min. Cell membranes are then recovered by centrifugation of the supernatant at 40000 g for 50 min. The pellet is resuspended in a solution containing 300 mM sucrose, 5 mM Tris-HCl, pH 7.5 and 20% glycerol. The membranes are frozen at −80 degrees C. until used for radioligand binding assays.

EXAMPLE 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The libation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least a 95% identity to a member selected from the group consisting of:
   (a) a polynucleotide encoding a polypeptide comprising The sequence of amino acids 1 to 416 of SEQ ID NO.2; and
   (b) the complement of (a).

2. The isolated polynucleotide of claim 1 wherein said member is (a).

3. The isolated polynucleotide of claim 1 wherein said polynucleotide encodes a polypeptide comprising the sequence of amino acids −24 to 416 of SEQ ID NO:2.

4. The isolated polynucleotide of claim 1 wherein said polynucleotide is identical to a polynucleotide encoding a polypeptide comprising the sequence of amino acids 1 to 416 of SEQ ID NO:2.

5. The isolated polynucleotide of claim 1, wherein the polynucleotide is DNA.

6. The isolated polynucleotide of claim 1 wherein said polynucleotide is identical to a polynucleotide encoding a polypeptide comprising the sequence of amino acids −24 to 416 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide.

12. The isolated polynucleotide of claim 11 comprising the sequence of nucleotides 156 to 1650 of SEQ ID NO.1.

13. The isolated polynucleotide of claim 11 comprising the sequence of nucleotides 228 to 1650 of SEQ ID NO.1.

14. The isolated polynucleotide of claim 11 comprising the polynucleotide of SEQ ID NO.1.

15. An isolated polynucleotide comprising a polynucleotide having at least a 95% identity to a member selected from the group consisting of:
   (a) a polynucleotide encoding the same mature polypeptide encoded by the human $GABA_A$ receptor epsilon subunit cDNA in ATCC Deposit No. 75842, and
   (b) the complement of (a).

16. The isolated polynucleotide of claim 15, wherein the member is (a).

17. The isolated polynucleotide of claim 15, wherein the member is (b).

18. The isolated polynucleotide of claim 15 comprising a polynucleotide which encodes the same mature polypeptide encoded by the human $GABA_A$ receptor epsilon subunit cDNA in ATCC Deposit No. 75842.

19. The isolated polynucleotide of claim 15 wherein said polynucleotide comprises DNA identical to the coding portion of the human $GABA_A$ receptor epsilon subunit cDNA in ATCC Deposit No. 75842 which encodes a mature polypeptide.

* * * * *

UNITED STATES PATENT AND TRADEMARK OFFICE
CERTIFICATE OF CORRECTION

PATENT NO. : 5,654,172
DATED : August 5, 1997
INVENTOR(S) : Yi Li, et al.

It is certified that error appears in the above-identified patent and that said Letters Patent is hereby corrected as shown below:

In Claim 15, line 47, for the Deposit No. "75842" should read --75810--.
In Claim 18, line 57, for the Deposit No. "75842" should read --75810--.
In Claim 19, line 61, for the Deposit No. "75842" should read --75810--.

Signed and Sealed this

Third Day of November, 1998

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1650 BASE PAIRS
( B ) TYPE: NUCLEIC ACID
( C ) STRANDEDNESS: SINGLE
( D ) TOPOLOGY: LINEAR ( i i ) MOLECULE TYPE: cDNA ( x i ) SEQUENCE DESCRIPTION: SEQ ID NO:1:

```
GGGACAGGGC  TGAGGATGAG  GAGAACCCTG  GGGACCCAGA  AGACCGTGCC  TTGCCCGGAA    60

GTCCTGCCTG  TAGGCCTGSS  GGACTTGCCC  TAACAGAGCC  TCAACAACTA  CCTGGTGATT   120

CCTACTTCAG  CCCCTTGGTG  TGAGCAGCTT  CTCAACATGA  ACTACAGCCT  CCACTTGGCC   180

TTCGTGTGTC  TGAGTCTCTT  CACTGAGAGG  ATGTGCATCC  AGGGGAGTCA  GTTCAACGTC   240

GAGGTCGGCA  GAAGTGACAA  GCTTTCCCTG  CCTGGCTTTG  AGAACCTCAC  AGCAGGATAT   300

AACAAATTTC  TCAGGCCCAA  TTTTGGTGGA  GAACCCGTAC  AGATAGCGCT  GACTCTGGAC   360

ATTGCAAGTA  TCTCTAGCAT  TTCAGAGAGT  AACATGGACT  ACACAGCCAC  CATATACCTC   420

CGACAGCGCT  GGATGGACCA  GCGGCTGGTG  TTTGAAGGCA  ACAAGAGCTT  CACTCTGGAT   480

GCCCGCCTCG  TGGAGTTCCT  CTGGGTGCCA  GATACTTACA  TTGTGGAGTC  CAAGAAGTCC   540

TTCCTCCATG  AAGTCACTGT  GGGAAACAGG  CTCATCCGCC  TCTTCTCCAA  TGGCACGGTC   600
```

-continued

```
CTGTATGCCC TCAGAATCAC GACAACTGTT GCATGTAACA TGGATCTGTC TAAATACCCC 660
ATGGACACAC AGACATGCAA GTTGCAGCTG GAAAGCTGGG GCTATGATGG AAATGATGTG 720
GAGTTCACCT GGCTGAGAGG GAACGACTCT GTGCGTGGAC TGGAACACCT GCGGCTTGCT 780
CAGTACACCA TAGAGCGGTA TTTCACCTTA GTCACCAGAT CGCAGCAGGA GACAGGAAAT 840
TACACTAGAT TGGTCTTACA GTTGAGCTT CGGAGGAATG TTCTGTATTT CATTTTGGAA 900
ACCTACGTTC CTTCCACTTT CCTGGTGGTG TTGTCCTGGG TTCTGTATTT CATTTTGGAA 960
GATTCAGTCC CTGCAAGAAC CTGCATTGGA GTGACGACCG TGTTATCAAT GACCACACTG 1020
ATGATCGGGT CCCGCACTTC TCTTCCCAAC ACCAACTGCT TCATCAAGGC CATCGATGTG 1080
TACCTGGGGA TCTGCTTTAG CTTTGTGTTT GGGGCCTTGC TAGAATATGC AGTTGCTCAC 1140
TACAGTTCCT TACAGCAGAT GGCAGCCAAA GATAGGGGGA CAACAAAGGA AGTAGAAGAA 1200
GTCAGTATTA CTAATATCAT CAACAGCTCC ATCTCCAGCT TAAACGGAA GATCAGCTTT 1260
GCCAGCATTG AAATTTCCAG CGACAACGTT GACTACAGTG ACTTGACAAT GAAAACCAGC 1320
GACAAGTTCA AGTTTGTCTT CCGAGAAAAG ATGGGCAGGA TTGTTGATTA TTTCACAATT 1380
CAAAACCCCA GTAATGTTGA TCACTATTCC AAACTACTGT TTCCTTTGAT TTTTAGTCTA 1440
GCCAATGTAT TTTACTGGGC ATACTACATG TATTTTGAG TCAATGTTAA ATTTCTTGCA 1500
TGCCATAGGT CTTCAACAGG ACAAGATAAT GATGTAAATG GTATTTTAGG CCAAGTGTGC 1560
ACCCACATCC AATGGTGCTA CAAGTGACTG AAATAATATT TGAGTCTTTC TGCTCAAAGA 1620
ATGAAGCTCC AACCATTGTT CTAAGCTGTG                                  1650
```

( 2 ) INFORMATION FOR SEQ ID NO:2:

( i ) SEQUENCE CHARACTERISTICS:
        ( A ) LENGTH: 440 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Asn Tyr Ser Leu His Leu Ala Phe Val Cys Leu Ser Leu Phe
                -20              -15                  -10

Thr Glu Arg Met Cys Ile Gln Gly Ser Gln Phe Asn Val Glu Val
                -5                1                    5

Gly Arg Ser Asp Lys Leu Ser Leu Pro Gly Phe Glu Asn Leu Thr
                10               15                   20

Ala Gly Tyr Asn Lys Phe Leu Arg Pro Asn Phe Gly Gly Glu Pro
                25               30                   35

Val Gln Ile Ala Leu Thr Leu Asp Ile Ala Ser Ile Ser Ser Ile
                40               45                   50

Ser Glu Ser Asn Met Asp Tyr Thr Ala Thr Ile Tyr Leu Arg Gln
                55               60                   65

Arg Trp Met Asp Gln Arg Leu Val Phe Glu Gly Asn Lys Ser Phe
                70               75                   80

Thr Leu Asp Ala Arg Leu Val Glu Phe Leu Trp Val Pro Asp Thr
                85               90                   95

Tyr Ile Val Glu Ser Lys Lys Ser Phe Leu His Glu Val Thr Val
                100              105                  110

Gly Asn Arg Leu Ile Arg Leu Phe Ser Asn Gly Thr Val Leu Tyr
                115              120                  125

Ala Leu Arg Ile Thr Thr Thr Val Ala Cys Asn Met Asp Leu Ser
```

|   |   |   | 130 |   |   |   | 135 |   |   |   | 140 |   |
|---|---|---|---|---|---|---|---|---|---|---|---|---|
| Lys | Tyr | Pro | Met | Asp | Thr | Gln | Thr | Cys | Lys | Leu | Gln | Leu | Glu | Ser |
|   |   |   | 145 |   |   |   | 150 |   |   |   | 155 |   |
| Trp | Gly | Tyr | Asp | Gly | Asn | Asp | Val | Glu | Phe | Thr | Trp | Leu | Arg | Gly |
|   |   |   | 160 |   |   |   | 165 |   |   |   | 170 |   |
| Asn | Asp | Ser | Val | Arg | Gly | Leu | Glu | His | Leu | Arg | Leu | Ala | Gln | Tyr |
|   |   |   | 175 |   |   |   | 180 |   |   |   | 185 |   |
| Thr | Ile | Glu | Arg | Tyr | Phe | Thr | Leu | Val | Thr | Arg | Ser | Gln | Gln | Glu |
|   |   |   | 190 |   |   |   | 195 |   |   |   | 200 |   |
| Thr | Gly | Asn | Tyr | Thr | Arg | Leu | Val | Leu | Gln | Phe | Glu | Leu | Arg | Arg |
|   |   |   | 205 |   |   |   | 210 |   |   |   | 215 |   |
| Asn | Val | Leu | Tyr | Phe | Ile | Leu | Glu | Thr | Tyr | Val | Pro | Ser | Thr | Phe |
|   |   |   | 220 |   |   |   | 225 |   |   |   | 230 |   |
| Leu | Val | Val | Leu | Ser | Trp | Val | Ser | Phe | Trp | Ile | Ser | Leu | Asp | Ser |
|   |   |   | 235 |   |   |   | 240 |   |   |   | 245 |   |
| Val | Pro | Ala | Arg | Thr | Cys | Ile | Gly | Val | Thr | Thr | Val | Leu | Ser | Met |
|   |   |   | 250 |   |   |   | 255 |   |   |   | 260 |   |
| Thr | Thr | Leu | Met | Ile | Gly | Ser | Arg | Thr | Ser | Leu | Pro | Asn | Thr | Asn |
|   |   |   | 265 |   |   |   | 270 |   |   |   | 275 |   |
| Cys | Phe | Ile | Lys | Ala | Ile | Asp | Val | Tyr | Leu | Gly | Ile | Cys | Phe | Ser |
|   |   |   | 280 |   |   |   | 285 |   |   |   | 290 |   |
| Phe | Val | Phe | Gly | Ala | Leu | Leu | Glu | Tyr | Ala | Val | Ala | His | Tyr | Ser |
|   |   |   | 295 |   |   |   | 300 |   |   |   | 305 |   |
| Ser | Leu | Gln | Gln | Met | Ala | Ala | Lys | Asp | Arg | Gly | Thr | Thr | Lys | Glu |
|   |   |   | 310 |   |   |   | 315 |   |   |   | 320 |   |
| Val | Glu | Glu | Val | Ser | Ile | Thr | Asn | Ile | Ile | Asn | Ser | Ser | Ile | Ser |
|   |   |   | 325 |   |   |   | 330 |   |   |   | 335 |   |
| Ser | Phe | Lys | Arg | Lys | Ile | Ser | Phe | Ala | Ser | Ile | Glu | Ile | Ser | Ser |
|   |   |   | 340 |   |   |   | 345 |   |   |   | 350 |   |
| Asp | Asn | Val | Asp | Tyr | Ser | Asp | Leu | Thr | Met | Lys | Thr | Ser | Asp | Lys |
|   |   |   | 355 |   |   |   | 360 |   |   |   | 365 |   |
| Phe | Lys | Phe | Val | Phe | Arg | Glu | Lys | Met | Gly | Arg | Ile | Val | Asp | Tyr |
|   |   |   | 370 |   |   |   | 375 |   |   |   | 380 |   |
| Phe | Thr | Ile | Gln | Asn | Pro | Ser | Asn | Val | Asp | His | Tyr | Ser | Lys | Leu |
|   |   |   | 385 |   |   |   | 390 |   |   |   | 395 |   |
| Leu | Phe | Pro | Leu | Ile | Phe | Met | Leu | Ala | Asn | Val | Phe | Tyr | Trp | Ala |
|   |   |   | 400 |   |   |   | 405 |   |   |   | 410 |   |
| Tyr | Tyr | Met | Tyr | Phe |
|   |   |   | 415 |

( 2 ) INFORMATION FOR SEQ ID NO:3:

( i ) SEQUENCE CHARACTERISTICS:
        ( A ) LENGTH: 467 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:3:

| Met | Ser | Ser | Pro | Asn | Ile | Trp | Ser | Thr | Gly | Ser | Ser | Val | Tyr | Ser |
|---|---|---|---|---|---|---|---|---|---|---|---|---|---|---|
|   |   |   |   | 5 |   |   |   |   | 10 |   |   |   |   | 15 |
| Thr | Pro | Val | Phe | Ser | Gln | Lys | Met | Thr | Val | Trp | Ile | Leu | Leu | Leu |
|   |   |   |   | 20 |   |   |   |   | 25 |   |   |   |   | 30 |
| Leu | Ser | Leu | Tyr | Pro | Gly | Phe | Thr | Ser | Gln | Lys | Ser | Asp | Asp | Asp |
|   |   |   |   | 35 |   |   |   |   | 40 |   |   |   |   | 45 |

-continued

| | | | | | | | | | | | | |
|---|---|---|---|---|---|---|---|---|---|---|---|---|
| Tyr | Glu | Asp | Tyr | Ala | Ser | Asn | Lys | Thr | Trp | Val | Leu | Thr | Pro | Lys |
| | | | | 50 | | | | 55 | | | | | | 60 |
| Val | Pro | Glu | Gly | Asp | Val | Thr | Val | Ile | Leu | Asn | Asn | Leu | Leu | Glu |
| | | | | 65 | | | | 70 | | | | | | 75 |
| Gly | Tyr | Asp | Asn | Lys | Leu | Arg | Pro | Asp | Ile | Gly | Val | Lys | Pro | Thr |
| | | | | 80 | | | | 85 | | | | | | 90 |
| Leu | Ile | His | Thr | Asp | Met | Tyr | Val | Asn | Ser | Ile | Gly | Pro | Val | Asn |
| | | | | 95 | | | | 100 | | | | | | 105 |
| Ala | Ile | Asn | Met | Glu | Tyr | Thr | Ile | Asp | Ile | Phe | Phe | Ala | Gln | Met |
| | | | | 110 | | | | 115 | | | | | | 120 |
| Trp | Tyr | Asp | Arg | Arg | Leu | Lys | Phe | Asn | Ser | Thr | Ile | Lys | Val | Leu |
| | | | | 125 | | | | 130 | | | | | | 135 |
| Arg | Leu | Asn | Ser | Asn | Met | Val | Gly | Lys | Ile | Trp | Ile | Pro | Asp | Thr |
| | | | | 140 | | | | 145 | | | | | | 150 |
| Phe | Phe | Arg | Asn | Ser | Lys | Lys | Ala | Asp | Ala | His | Trp | Ile | Thr | Thr |
| | | | | 155 | | | | 160 | | | | | | 165 |
| Pro | Asn | Arg | Met | Leu | Arg | Ile | Trp | Asn | Asp | Gly | Arg | Val | Leu | Tyr |
| | | | | 170 | | | | 175 | | | | | | 180 |
| Ser | Leu | Arg | Leu | Thr | Ile | Asp | Ala | Glu | Cys | Gln | Leu | Gln | Leu | His |
| | | | | 185 | | | | 190 | | | | | | 195 |
| Asn | Phe | Pro | Met | Asp | Glu | His | Ser | Cys | Pro | Leu | Glu | Phe | Ser | Ser |
| | | | | 200 | | | | 205 | | | | | | 210 |
| Tyr | Gly | Tyr | Pro | Arg | Glu | Glu | Ile | Val | Tyr | Gln | Trp | Lys | Arg | Ser |
| | | | | 215 | | | | 220 | | | | | | 225 |
| Ser | Val | Glu | Val | Gly | Asp | Thr | Arg | Ser | Trp | Arg | Leu | Tyr | Gln | Phe |
| | | | | 230 | | | | 235 | | | | | | 240 |
| Ser | Phe | Val | Gly | Leu | Arg | Asn | Thr | Thr | Glu | Val | Val | Lys | Thr | Thr |
| | | | | 245 | | | | 250 | | | | | | 255 |
| Ser | Gly | Asp | Tyr | Val | Val | Met | Ser | Val | Tyr | Phe | Asp | Leu | Ser | Arg |
| | | | | 260 | | | | 265 | | | | | | 270 |
| Arg | Met | Gly | Tyr | Phe | Thr | Ile | Gln | Thr | Tyr | Ile | Pro | Cys | Thr | Leu |
| | | | | 275 | | | | 280 | | | | | | 285 |
| Ile | Val | Val | Leu | Ser | Trp | Val | Ser | Phe | Trp | Ile | Asn | Lys | Asp | Ala |
| | | | | 290 | | | | 295 | | | | | | 300 |
| Val | Pro | Ala | Arg | Thr | Ser | Leu | Gly | Ile | Thr | Thr | Val | Leu | Thr | Met |
| | | | | 305 | | | | 310 | | | | | | 315 |
| Thr | Thr | Leu | Ser | Thr | Ile | Ala | Arg | Lys | Ser | Leu | Pro | Lys | Val | Ser |
| | | | | 320 | | | | 325 | | | | | | 330 |
| Tyr | Val | Thr | Ala | Met | Asp | Leu | Phe | Val | Ser | Val | Cys | Phe | Ile | Phe |
| | | | | 335 | | | | 340 | | | | | | 345 |
| Val | Phe | Ser | Ala | Leu | Val | Glu | Tyr | Gly | Thr | Leu | His | Tyr | Phe | Val |
| | | | | 350 | | | | 355 | | | | | | 360 |
| Ser | Asn | Arg | Lys | Pro | Ser | Lys | Asp | Lys | Asp | Lys | Lys | Lys | Lys | Asn |
| | | | | 365 | | | | 370 | | | | | | 375 |
| Pro | Ala | Pro | Thr | Ile | Asp | Ile | Arg | Pro | Arg | Ser | Ala | Thr | Ile | Gln |
| | | | | 380 | | | | 385 | | | | | | 390 |
| Met | Asn | Asn | Ala | Thr | His | Leu | Gln | Glu | Arg | Asp | Glu | Glu | Tyr | Gly |
| | | | | 395 | | | | 400 | | | | | | 405 |
| Tyr | Glu | Cys | Leu | Asp | Gly | Lys | Asp | Cys | Ala | Ser | Phe | Phe | Cys | Cys |
| | | | | 410 | | | | 415 | | | | | | 420 |
| Phe | Glu | Asp | Cys | Arg | Thr | Gly | Ala | Trp | Arg | His | Gly | Arg | Ile | His |
| | | | | 425 | | | | 430 | | | | | | 435 |
| Ile | Arg | Ile | Ala | Lys | Met | Asp | Ser | Tyr | Ala | Arg | Ile | Phe | Phe | Pro |
| | | | | 440 | | | | 445 | | | | | | 450 |

```
Thr Ala Phe Cys Leu Phe Asn Leu Val Tyr Trp Val Ser Tyr Leu
            455                 460                 465

Tyr Leu
```

(2) INFORMATION FOR SEQ ID NO:4:

(i) SEQUENCE CHARACTERISTICS:
  (A) LENGTH: 474 AMINO ACIDS
  (B) TYPE: AMINO ACID
  (C) STRANDEDNESS:
  (D) TOPOLOGY: LINEAR (ii) MOLECULE TYPE: PROTEIN (xi) SEQUENCE DESCRIPTION: SEQ ID NO:4:

```
Met Trp Thr Val Gln Asn Arg Glu Ser Leu Gly Leu Leu Ser Phe
              5                  10                  15

Pro Val Met Ile Thr Met Val Cys Cys Ala His Ser Thr Asn Glu
             20                  25                  30

Pro Ser Asn Met Pro Tyr Val Lys Glu Thr Val Asp Arg Leu Leu
             35                  40                  45

Lys Gly Tyr Asp Ile Arg Leu Arg Pro Asp Phe Gly Gly Pro Pro
             50                  55                  60

Val Asp Val Gly Met Arg Ile Asp Val Ala Ser Ile Asp Met Val
             65                  70                  75

Ser Glu Val Asn Met Asp Tyr Thr Leu Thr Met Tyr Phe Gln Gln
             80                  85                  90

Ser Trp Lys Asp Lys Arg Leu Ser Tyr Ser Gly Ile Pro Leu Asn
             95                 100                 105

Leu Thr Leu Asp Asn Arg Val Ala Asp Gln Leu Trp Val Pro Asp
            110                 115                 120

Thr Tyr Phe Leu Asn Asp Lys Lys Ser Phe Val His Gly Val Thr
            125                 130                 135

Val Lys Asn Arg Met Ile Arg Leu His Pro Asp Gly Thr Val Leu
            140                 145                 150

Tyr Gly Leu Arg Ile Thr Thr Thr Ala Ala Cys Met Met Asp Leu
            155                 160                 165

Arg Arg Tyr Pro Leu Asp Glu Gln Asn Cys Thr Leu Glu Ile Glu
            170                 175                 180

Ser Tyr Gly Tyr Thr Thr Asp Asp Ile Glu Phe Tyr Trp Asn Gly
            185                 190                 195

Gly Glu Gly Ala Val Thr Gly Val Asn Lys Ile Glu Leu Pro Gln
            200                 205                 210

Phe Ser Ile Val Asp Tyr Lys Met Val Ser Lys Lys Val Glu Phe
            215                 220                 225

Thr Thr Gly Ala Tyr Pro Arg Leu Ser Leu Ser Phe Arg Leu Lys
            230                 235                 240

Arg Asn Ile Gly Tyr Phe Ile Leu Gln Thr Tyr Met Pro Ser Thr
            245                 250                 255

Leu Ile Thr Ile Leu Ser Trp Val Ser Phe Trp Ile Asn Tyr Asp
            260                 265                 270

Ala Ser Ala Ala Arg Val Ala Leu Gly Ile Thr Thr Val Leu Thr
            275                 280                 285

Met Thr Thr Ile Ser Thr His Leu Arg Glu Thr Leu Pro Lys Ile
            290                 295                 300

Pro Tyr Val Lys Ala Ile Asp Ile Tyr Leu Met Gly Cys Phe Val
```

|     |     |     |     | 305 |     |     |     | 310 |     |     |     | 315 |
| --- | --- | --- | --- | --- | --- | --- | --- | --- | --- | --- | --- | --- |
| Phe | Val | Phe | Leu | Ala | Leu | Leu | Glu | Tyr | Ala | Phe | Val | Asn | Tyr | Ile |
|     |     |     |     | 320 |     |     |     | 325 |     |     |     | 330 |
| Phe | Phe | Gly | Lys | Gly | Pro | Gln | Lys | Lys | Gly | Ala | Ser | Lys | Gln | Asp |
|     |     |     |     | 335 |     |     |     | 340 |     |     |     | 345 |
| Gln | Ser | Ala | Asn | Glu | Lys | Asn | Lys | Leu | Glu | Met | Asn | Lys | Val | Gln |
|     |     |     |     | 350 |     |     |     | 355 |     |     |     | 360 |
| Val | Asp | Ala | His | Gly | Asn | Ile | Leu | Leu | Ser | Thr | Leu | Glu | Ile | Arg |
|     |     |     |     | 365 |     |     |     | 370 |     |     |     | 375 |
| Asn | Glu | Thr | Ser | Gly | Ser | Glu | Val | Leu | Thr | Ser | Val | Ser | Asp | Pro |
|     |     |     |     | 380 |     |     |     | 385 |     |     |     | 390 |
| Lys | Ala | Thr | Met | Tyr | Ser | Tyr | Asp | Ser | Ala | Ser | Ile | Gln | Tyr | Arg |
|     |     |     |     | 395 |     |     |     | 400 |     |     |     | 405 |
| Lys | Pro | Leu | Ser | Ser | Arg | Glu | Ala | Tyr | Gly | Arg | Ala | Leu | Asp | Arg |
|     |     |     |     | 410 |     |     |     | 415 |     |     |     | 420 |
| His | Gly | Val | Pro | Ser | Lys | Gly | Arg | Ile | Arg | Arg | Arg | Ala | Ser | Gln |
|     |     |     |     | 425 |     |     |     | 430 |     |     |     | 435 |
| Leu | Lys | Val | Lys | Ile | Pro | Asp | Leu | Thr | Asp | Val | Asn | Ser | Ile | Asp |
|     |     |     |     | 440 |     |     |     | 445 |     |     |     | 450 |
| Lys | Trp | Ser | Arg | Met | Phe | Phe | Pro | Ile | Thr | Phe | Ser | Leu | Phe | Asn |
|     |     |     |     | 455 |     |     |     | 460 |     |     |     | 465 |
| Val | Val | Tyr | Trp | Leu | Tyr | Tyr | Val | His |     |     |     |     |
|     |     |     |     | 470 |     |     |     |     |     |     |     |     |